United States Patent [19]

Oshlack et al.

[11] Patent Number: 5,286,493
[45] Date of Patent: Feb. 15, 1994

[54] STABILIZED CONTROLLED RELEASE FORMULATIONS HAVING ACRYLIC POLYMER COATING

[75] Inventors: Benjamin Oshlack, New York, N.Y.; Mark Chasin, Manalapan, N.J.; Frank Pedi, Jr., Yorktown Heights, N.Y.

[73] Assignee: Euroceltique, S.A., Luxembourg

[21] Appl. No.: 826,084

[22] Filed: Jan. 27, 1992

[51] Int. Cl.$^5$ .................... A61K 9/62; A61K 9/00
[52] U.S. Cl. .................... 424/468; 424/482; 424/497; 424/483
[58] Field of Search .................... 424/78.17, 472, 486, 424/468, 482, 483, 497

[56] References Cited

U.S. PATENT DOCUMENTS

| | | | |
|---|---|---|---|
| 4,600,645 | 7/1986 | Ghebre-Sellassie | 424/482 |
| 4,728,513 | 3/1988 | Ventouras | 424/461 |
| 5,019,397 | 5/1991 | Wong et al. | 424/472 |
| 5,024,842 | 6/1991 | Edgren et al. | 424/472 |
| 5,068,110 | 11/1991 | Fawzi et al. | 424/462 |

FOREIGN PATENT DOCUMENTS 60-166608 8/1985 Japan .................... 424/472

*Primary Examiner*—Paul R. Michl
*Assistant Examiner*—Peter F. Kulkosky
*Attorney, Agent, or Firm*—Steinberg & Raskin

[57] ABSTRACT

A stabilized solid controlled release dosage form having a coating derived from an aqueous dispersion of an acrylic polymer is obtained by overcoating a substrate including a therapeutically active with an aqueous dispersion of the plasticized acrylic polymer and then curing the coated substrate at a temperature above the glass transition temperature of the plasticized acrylic polymer, until the coated dosage form attains a stabilized dissolution profile substantially unaffected by exposure to storage conditions of elevated temperature and/or elevated relative humidity.

35 Claims, No Drawings ered. Stability study requirements are covered, e.g., in the Good Manufacturing Practices (GMPs), the U.S.P., as well as in New Drug Applications (NDAs) and Investigational New Drug Applications (INDs).

STABILIZED CONTROLLED RELEASE FORMULATIONS HAVING ACRYLIC POLYMER COATING

BACKGROUND OF THE INVENTION

An important aspect of all forms of low dosage forms is related to the stability of the same. The stability of a pharmaceutical dosage form is related to maintaining its physical, chemical, microbiological, therapeutic, and toxicological properties when stored, i.e., in a particular container and environment. Stability study requirements are covered, e.g., in the Good Manufacturing Practices (GMPs), the U.S.P., as well as in New Drug Applications (NDAs) and Investigational New Drug Applications (INDs).

The ingredients used in sustained release dosage formulations often present special problems with regard to their physical stability during storage. For example, waxes which have been used in such formulations are known to undergo physical alterations on prolonged standing, thus precautions are taken to stabilize them at the time of manufacture or to prevent the change from occurring. Fats and waxy materials when used in purified states are known to crystallize in unstable forms, causing unpredictable variations in availability rates during stability testing at the time of manufacture and during later storage.

It is known that certain strategies can be undertaken to obtain stabilized controlled release formulations in many cases, such as insuring that the individual ingredients are in a stable form before they are incorporated into the product, and that processing does not change this condition, retarding the instability by including additional additives, and inducing the individual ingredients of the dosage form to reach a stable state before the product is finally completed.

It is also recognized that the moisture content of the product can also influence the stability of the product. Changes in the hydration level of a polymeric film, such as the ethyl celluloses, can alter the rate of water permeation and drug availability. Also, binders such as acacia are known to become less soluble when exposed to moisture and heat. However, moisture content of a product can be controlled fairly successfully by controls in the processing method and proper packaging of the product.

Hydrophobic polymers such as certain cellulose derivatives, zein, acrylic resins, waxes, higher aliphatic alcohols, and polylactic and polyglycolic acids have been used in the prior art to develop controlled release dosage forms. Methods of using these polymers to develop controlled release dosage forms such as tablets, capsules, suppositories, spheroids, beads or microspheres are to overcoat the individual dosage units with these hydrophobic polymers. It is known in the prior art that these hydrophobic coatings can be applied either from a solution, suspension or dry. Since most of these polymers have a low solubility in water, they are usually applied by dissolving the polymer in an organic solvent and spraying the solution onto the individual drug forms (such as beads or tablets) and evaporating off the solvent.

Aqueous dispersions of hydrophobic polymers have been used in the prior art to coat pharmaceutical dosage forms for aesthetic reasons such as film coating tablets or beads or for taste-masking. However, these dosage forms are used for immediate release administration of the active drug contained in the dosage form.

Attempts to prepare stable controlled release pharmaceutical formulations using aqueous dispersions of hydrophobic polymers have been unsuccessful due to stability problems.

Therefore, it is desirable to prepare a controlled release formulation prepared from an aqueous dispersion of a hydrophobic polymer. However, to date, attempts to prepare stable controlled release pharmaceutical formulations using aqueous dispersions of hydrophobic polymers have been unsuccessful due to stability problems.

In particular, when coating these pharmaceutical forms using aqueous polymeric dispersions to obtain a desired release profile of the active drug(s) over several hours or longer, it is known in the art that the dissolution release profile changes on ageing. This was recently demonstrated by Munday, et al., Drug Devel. and Indus. Phar., 17 (15) 2135-2143 (1991), which reported the effect of storing theophylline mini-tablets film coated with ethyl cellulose with PEG (2:1 ratio; total coating=3% w/w), ethyl cellulose with Eudragit® L (2:1 ratio; total coating=3% w/w); and Eudragit® RL (amount of coating=1.5% w/w) at varying temperatures and relative humidities upon the rate of drug release. Samples were subjected to isothermal storage at 28° C., 35° C. and 45° C. with the relative humidity (RH) maintained between 55-60%, under cyclic conditions of 45° C. at 55% RH for 24 hours, then at 28° C. and 20% RH for 24 hours, and then at 5° C. and 10% RH for 24 hours, after which the cycle was repeated, and alternating conditions every 24 hours between 45° C. and 55% RH and 28° C. and 0% RH. The aging process brought about by storage under the above stress conditions impeded dissolution, irrespective of the nature of the polymeric film. The greatest reduction in release rate was said to occur in the first 21 days (isothermal storage) after coating.

This instability problem is known to not exist when the polymers are applied from organic solvent solution. The use of organic solvents in the preparation of polymer coatings is considered problematic as the formulations have inherent problems with regard to flammability, carcinogenicity, environmental concerns, and safety in general.

Furthermore, attempts to prepare controlled release pharmaceutical formulations using organic coatings have been largely unsuccessful due to stability problems, the rate of drug release being changed upon storage.

For example, it has been considered desirable in the art to prepare a controlled release formulation which utilizes a retardant coating derived from an aqueous acrylic polymer dispersion, such as Eudragit®, commercially available from Rohm Pharma. However, to date it has not been possible to obtain a controlled release formulation which is stable under various storage conditions.

More particularly, it is known that a controlled release coating comprising Eudragit® is not stable when cured according to recommended curing conditions by the manufacturer of 45° C. for 2 hours.

OBJECTS AND SUMMARY OF THE INVENTION

It is therefore an object of the present invention to provide a controlled release dosage form for oral administration which has a controlled release coating derived from an aqueous acrylic polymer dispersion, such that an essentially stabile dissolution profile of medicament is obtained under various storage conditions.

It is a further object of the present invention to provide a controlled release dosage form prepared with an overcoat derived from an aqueous dispersion of an acrylic resin which is stable under stressed conditions, including extended periods of high temperature and high humidity.

These objects and others have been accomplished by the present invention, which relates to a solid dosage form which has a controlled release overcoat derived from an aqueous dispersion of an acrylic resin which provides a substantially stable release pattern of a therapeutically active agent(s) contained therein.

The present invention further relates to the surprising discovery that when the coated formulation is exposed to certain elevated or "stressed" conditions of temperature and humidity for a certain amount of time, a desired endpoint may be attained whereat the release rate of the therapeutically active agent does not substantially change upon ageing under a wide range of temperature and/or humidity conditions. This surprising discovery makes it possible to the controlled release coatings of the present invention for a variety of pharmaceutical dosage forms to produce stable controlled release pharmaceutical products.

The present invention is also related to a solid dosage form comprising a core comprising a therapeutically active agent and an overcoating derived from an aqueous dispersion of an acrylic resin in an amount sufficient to obtain a controlled release of the therapeutically active agent when the dosage form is exposed to aqueous solutions, e.g. gastric fluid. The solid dosage form is cured after the overcoating is applied such that the release of the therapeutically active agent is substantially unchanged by exposure to temperature and/or humidity elevated above ambient conditions.

The present invention is also related to a stabilized controlled release solid dosage form for oral administration, comprising a plurality of inert pharmaceutically acceptable beads coated with a therapeutically active agent, and an overcoat of an acrylic resin having a suitable thickness to obtain a controlled release of said therapeutically active agent when the solid dosage form is exposed to aqueous solutions. The coated beads are cured for an extended period of time at a temperature above the glass transition temperature (Tg) of the plasticized acrylic polymer to attain a finished product which has a dissolution profile which is substantially unchanged by exposure to storage conditions of temperature and/or humidity elevated above ambient conditions.

The present invention is further related to a stabilized solid controlled dosage form comprising a therapeutically active agent overcoated with a plasticized acrylic polymer, the coated dosage form being cured at an effective temperature above the Tg of the plasticized acrylic polymer for such a time period that a stabilized drug dissolution profile substantially unchanged by exposure to storage conditions of temperature and/or relative humidity elevated above ambient conditions is obtained.

The present invention is also related to a method for obtaining a stabilized controlled release formulation comprising a substrate coated with a plasticized acrylic polymer. The method includes the steps of preparing an aqueous dispersion of the acrylic polymer and preferably plasticized, preparing a substrate comprising a therapeutically active agent, overcoating the substrate with a sufficient amount of the dispersion of acrylic polymer to obtain a predetermined controlled release of the therapeutically active agent when the coated particles are exposed to aqueous solutions, and curing the coated substrate at an effective temperature above the Tg of the plasticized acrylic polymer for such a time period that an endpoint is achieved at which the coated substrate attains a drug dissolution profile which is substantially unchanged by exposure to storage conditions of elevated or changing temperature and/or humidity.

The term "stabilized" and the phrase "substantially unchanged" with regard to the dissolution profile of the formulations of the present invention is defined for purposes of the present invention as meaning that the formulation reproducibly attains a dissolution profile which, even after exposure to accelerated storage conditions, falls within a certain range of drug release over time deemed to be within acceptable limits by the FDA or a corresponding regulatory agency. Such an acceptable range is typically determined on a case-by-case basis, depending upon the particular drug in question, the desired dosage regimen, etc.

In a further embodiment, the method further includes the step of determining the endpoint for a particular formulation by exposing the formulation to various stages of the above-mentioned curing and obtaining dissolution profiles for the formulation until the dissolution profiles of the formulation are substantially stabilized. The formulation is then modified, if necessary, to obtain a desired dissolution profile of the therapeutically active agent based on the end point.

DETAILED DESCRIPTION

In certain preferred embodiments of the present invention, the acrylic polymer comprising the controlled release coating is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a controlled release formulation, it is usually necessary to overcoat the substrate comprising the therapeutically active agent with a sufficient amount of the aqueous dispersion of acrylic polymer to obtain a weight gain level from about 5 to about 15 percent, although the overcoat may be lesser or greater depending upon the physical properties of the therapeutically active agent and the desired release rate, the inclusion of plasticizer in the aqueous dispersion of acrylic polymer the manner of incorporation of the same, for example.

An example of a suitable controlled release formulation pursuant to the present invention will provide a dissolution rate in vitro of the dosage form, when measured by the USP Paddle Method at 100 rpm in 900 ml aqueous buffer (pH between 1.6 and 7.2) at 37° C., is between 12.5 and 42.5% (by wt) therapeutically active agent released after 1 hour, between 25 and 55% (by wt) released after 2 hours, between 45 and 75% (by wt) released after 4 hours and greater than about 55% (by wt) released after 6 hours. This example is, of course, not intended to be limiting in any manner whatsoever.

In order to obtain a desirable dissolution profile for a given therapeutically active agent, such as that detailed above, it may be necessary to incorporate two or more ammonio methacrylate copolymers having differing physical properties. For example, it is known that by changing the molar ratio of the quaternary ammonium groups to the neutral (meth)acrylic esters, the permeability properties of the resultant coating can be modified.

In a preferred embodiment of the present invention, the acrylic coating is derived from a mixture of two acrylic resin lacquers used in the form of aqueous dispersions, commercially available from Rohm Pharma under the Tradename Eudragit ® RL 30 D and Eudragit ® RS 30 D, respectively. Eudragit ® RL 30 D and Eudragit ® RS 30 D are copolymers of acrylic and methacrylic esters with a low content of quaternary ammonium groups, the molar ratio of ammonium groups to the remaining neutral (meth)acrylic esters being 1:20 in Eudragit ® RL 30 D and 1:40 in Eudragit ® RS 30 D. The mean molecular weight is about 150,000. The code designations RL (high permeability) and RS (low permeability) refer to the permeability properties of these agents. Eudragit ® RL/RS mixtures are insoluble in water and in digestive fluids. However, coatings formed from the same are swellable and permeable in aqueous solutions and digestive fluids.

The Eudragit ® RL/RS dispersions of the present invention may be mixed together in any desired ratio in order to ultimately obtain a controlled release formulation having a desirable dissolution profile. Desirable controlled release formulations may be obtained, for instance, from a retardant coating derived from 100% Eudragit ® RL, 50% Eudragit ® RL and 50% Eudragit ® RS, and 10% Eudragit ® RL:Eudragit ® 90% RS.

In addition to modifying the dissolution profile by altering the relative amounts of different acrylic resin lacquers, the dissolution profile of the ultimate product may also be modified, for example, by increasing or decreasing the thickness of the retardant coating.

The aqueous dispersions of acrylic polymers used as coatings in the present invention may be used in conjunction with tablets, spheroids (or beads), microspheres, seeds, pellets, ion-exchange resin beads, and other multi-particulate systems in order to obtain a desired controlled release of the therapeutically active agent. Granules, spheroids, or pellets, etc., prepared in accordance with the present invention can be presented in a capsule or in any other suitable dosage form.

The coating formulations of the present invention should be capable of producing a strong, continuous film that is smooth and elegant, capable of supporting pigments and other coating additives, non-toxic, inert, and tack-free.

It is preferred that the acrylic coatings used in the present invention include an effective amount of a suitable plasticizing agent, as it has been found that the use of a plasticizer will further improve the physical properties of the film. For example, the use of a plasticizer may improve the film elasticity and lower the film-forming temperature of the dispersion. The plasticization of the acrylic resin may be accomplished either by so-called "internal plasticization" and "external plasticization."

Internal plasticization usually pertains directly to molecular modifications of the polymer during its manufacture, e.g., by copolymerization, such as altering and/or substituting functional groups, controlling the number of side chains, or controlling the length of the polymer. Such techniques are usually not performed by the formulator of the coating solution.

External plasticization involves the addition of a material to a film solution so that the requisite changes in film properties of the dry film can be achieved.

The suitability of a plasticizer depends on its affinity or solvating power for the polymer and its effectiveness at interfering with polymer-polymer attachments. Such activity imparts the desired flexibility by relieving molecular rigidity.

Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Most preferably, about 20% plasticizer is included in the aqueous dispersion of acrylic polymer.

An important parameter in the determination of a suitable plasticizer for a polymer is related to the glass transition temperature (Tg) of the polymer. The glass transition temperature is related to the temperature or temperature range where there is a fundamental change in the physical properties of the polymer. This change does not reflect a change in state, but rather a change in the macromolecular mobility of the polymer. Below the Tg, the polymer chain mobility is severely restricted. Thus, for a given polymer, if its Tg is above room temperature, the polymer will behave as a glass, being hard, non-pliable and rather brittle, properties which could be somewhat restrictive in film coating since the coated dosage form may be subjected to a certain amount of external stress.

Incorporation of suitable plasticizers into the polymer matrix effectively reduces the Tg, so that under ambient conditions the films are softer, more pliable and often stronger, and thus better able to resist mechanical stress. Other aspects of suitable plasticizers include the ability of the plasticizer to act as a good "swelling agent" for the ethylcellulose, and the insolubility of the plasticizer in water.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit ® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

The stabilized controlled release formulations of the present invention slowly release the therapeutically active agent, e.g., when ingested and exposed to gastric fluids. The controlled release profile of the formulations of the invention can be altered, for example, by varying the amount of overcoating, altering the manner in which the plasticizer is added, by varying the amount of plasticizer relative to acrylic resin, by the inclusion of additional ingredients or excipients, by altering the method of manufacture, etc.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), anti-inflammatory agents (e.g., naproxyn, diclofenac, indomethacin, ibuprofen, acetaminophen, aspirin, sulindac), gastro-intestinals and anti-emetics (e.g., metoclopramide), anti-epileptics (e.g., phenytoin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), anti-spasmodics (e.g. atropine, scopolamine), hormones (e.g., insulin, leparin), diuretics (e.g., eltacrymic acid, bendrofluazide), anti-hypotensives (e.g., propranolol, clonidine), bronchodilators (e.g., albuterol), anti-inflammatory steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, antacids, vitamins, stimulants (including appetite suppressants such as phenylpropanolamine). The above list is not meant to be exclusive.

In certain preferred embodiments, the therapeutically active agent comprises hydromorphone, oxycodone, dihydrocodeine, codeine, hydromorphone, dihydromorphine, morphine, buprenorphine, salts of any of the foregoing. and mixtures of any of the foregoing, and the like. In other preferred embodiments, the therapeutically active agent comprises theophylline.

When the dispersion of acrylic resin is used to coat inert pharmaceutical beads such as nu pariel 18/20 beads, a plurality of the resultant stabilized solid controlled release beads may thereafter be placed in a gelatin capsule in an amount sufficient to provide an effective controlled release dose when ingested and contacted by gastric fluid. In this embodiment, beads coated with a therapeutically active agent are prepared, e.g. by dissolving the therapeutically active agent in water and then spraying the solution onto a substrate, for example, nu pariel 18/20 beads, using a Wurster insert. Optionally, additional ingredients are also added prior to coating the beads in order to assist the hydromorphone binding to the beads, and/or to color the solution, etc. For example, a product which includes hydroxypropyl methylcellulose, etc. with or without colorant may be added to the solution and the solution mixed (e.g., for about 1 hour) prior to application of the same onto the beads. The resultant coated substrate, in this example beads, may then be optionally overcoated with a barrier agent, to separate the therapeutically active agent from the acrylic coating. An example of a suitable barrier agent is one which comprises hydroxypropyl methylcellulose. However, any film-former known in the art may be used. It is preferred that the barrier agent does not affect the dissolution rate of the final product.

The hydromorphone, HPMC protected (optional) beads may then be overcoated with the acrylic polymer. The dispersion of acrylic polymer preferably further includes an effective amount of plasticizer, e.g. triethyl citrate. Pre-formulated dispersions of acrylic resins, such as various commercially available forms of Eudragit ®, such as Eudragit ® RS30D and Eudragit ® RL 30D.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the overcoat. Suitable ingredients for providing color to the formulation include titanium dioxide and color pigments, such as iron oxide pigments. The incorporation of pigments, may, however, increase the retard effect of the coating. Alternatively, any suitable method of providing color to the formulations of the present invention may be used.

The plasticized coating of acrylic polymer may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the coating to obtain a predetermined controlled release of the therapeutically active agent when said coated substrate is exposed to aqueous solutions, e.g. gastric fluid, is preferably applied, taking into account the physically characteristics of the therapeutically active agent, the manner of incorporation of the plasticizer, etc.

After coating with acrylic resin, a further overcoat of a film-former, such as Opadry ®, is optionally applied to the beads. This overcoat is provided, if at all, in order to substantially reduce agglomeration of the beads.

Next, the coated beads are cured in order to obtain a stabilized release rate of the therapeutically active agent.

Traditionally, curing has been carried out for Eudragit ® coated formulations, if at all, via a fluid bed at 45° C. for 2 hours after application. Such a standard curing is recommended by Rohm Pharma because it is above the glass transition temperature (Tg) of Eudragit ® RS 30 D plasticized with triethylcitrate at a 20% level of solids. This recommended curing does not stabilize the dissolution profile of the formulation upon storage, as will be demonstrated by the examples set forth herein.

The curing step pursuant to the present invention is accomplished by subjecting the coated substrate, e.g., beads, to a temperature greater than the Tg of the coating formulation and continuing the curing until an endpoint is reached at which the coated formulation attains a dissolution profile which is substantially unaffected by exposure to storage conditions of elevated temperature and/or humidity. Generally, the curing time is about 24 hours or more, and the curing temperature may be, for example, about 45° C. It has further been discovered in the present invention that it is not necessary to subject the coated substrate to humidity levels above ambient conditions during the curing step in order to achieve a stabilized end product.

One possible mechanism for the change in the dissolution profile of prior art products cured by the standard methods is that these products continue to cure during storage, and may never reach a stabilized end-point at which the product provides a substantially constant dissolution profile. In contrast, the cured products of the present invention provide a release rate of the therapeutically active agent which is substantially unaffected during storage by elevations in temperature and humidity.

In preferred embodiments of the present invention, the stabilized product is obtained by subjecting the coated substrate to oven curing at a temperature above the Tg of the plasticized acrylic polymer for the required time period, the optimum values for temperature and time for the particular formulation being determined experimentally.

In certain embodiments of the present invention, the stabilized product is obtained via an oven curing conducted at a temperature of about 45° C. for a time period from about 24 to about 48 hours. Thus, in certain embodiments, it may be preferable to cure the product for, e.g., 36 hours. In certain preferred embodiments, the product is cured for about 48 hours. It is also contemplated herein that certain products coated with the controlled release coating of the present invention may require a curing time longer than 48 hours, e.g. 60 hours or more.

When the controlled release coating of the present invention is to be applied to tablets, the tablet core (e.g. the substrate) may comprise the active agent along with any pharmaceutically accepted inert pharmaceutical filler (diluent) material, including but not limited to sucrose, dextrose, lactose, microcrystalline cellulose, xylitol, fructose, sorbitol, mixtures thereof and the like. Also, an effective amount of any generally accepted pharmaceutical lubricant, including the calcium or magnesium soaps may be added to the above-mentioned ingredients of the excipient prior to compression of the tablet core ingredients. Most preferred is magnesium stearate in an amount of about 0.5-3% by weight of the solid dosage form.

Tablets overcoated with a sufficient amount of the coating of acrylic resin to achieve a controlled release formulation pursuant to the present may be prepared and cured in similar fashion as explained above with regard to the preparation of beads. One skilled in the art will recognize that necessary curing conditions with regard to the particular elevated temperature, elevated humidity and time ranges necessary to obtain a stabilized product, will depend upon the particular formulation.

DETAILED DESCRIPTION OF THE PREFERRED EMBODIMENTS

The following examples illustrate various aspects of the present invention. They are not to be construed to limit the claims in any manner whatsoever.

EXAMPLE 1

Preparation of Hydromorphone Beads

Hydromorphone beads were prepared by dissolving hydromorphone HCl in water, adding Opadry ® Y-5-1442, light pink (a product commercially available from Coloron, West Point, Pa., which contains hydroxypropyl methylcellulose, hydroxypropyl cellulose, titanium dioxide, polyethylene glycol and D&C Red No. 30 Aluminum Lake), 20% w/w, and mixing for about 1 hour, and then spraying onto nu pariel 18/20 beads using a Wurster insert. The resultant preparation had the formula set forth in Table 1 below:

TABLE 1

| Ingredients | Percent (by wt) | Amt/Unit (mg) |
|---|---|---|
| Hydromorphone HCl | 5.0% | 4.0 mg |
| Nu Pariel 18/20 | 92.5% | 74.0 mg |
| Opadry ® Lt. Pink Y-5-1442 | 2.5% | 2.0 mg |
|  | 100.0% | 80.0 mg |

EXAMPLE 2

Retardant Coating - No Curing Step

In Example 2, hydromorphone beads prepared in accordance with Example 1 were overcoated with Eudragit ® RS 30D to a 5% weight gain as set forth in Table 2 below. No terminal drying was conducted

TABLE 2

| Ingredients | Percent (by wt) | Amt/Unit (mg) |
|---|---|---|
| Hydromorphone beads | 92.59 | 80 |
| Eudragit ® RS30D | 4.63 | 4 |
| Citroflex 2 (triethyl citrate) | 0.93 | 0.8 |
| Talc | 1.85 | 1.6 |
| Purified water |  | qs |
|  | 100 | 86.4 |

The hydromorphone beads were tested for initial dissolution, and then stored for one month under accelerated conditions of 37° C./80% RH (RH=relative humidity). After one month, the beads were found to have agglomerated.

Dissolution tests were carried out via the USP Basket Method, 37° C., 100 RPM, first hour 700 ml gastric fluid at pH 1.2, then changed to 900 ml at 7.5. The dissolution was conducted by placing an open capsule containing an appropriate weight of beads into a vessel. The results are set forth in Table 3 below:

TABLE 3

Hydromorphone HCl 12 mg Controlled Released Capsules Stability Performance Data

| Time | Hydromorphone HCl (mg) | Average Fill Wt (mg) | 1 hr | 2 hr | 4 hr | 8 hr | 12 hr | 18 hr | 24 hr |
|---|---|---|---|---|---|---|---|---|---|
| Initial | 12.34 | 259.2 | 1.5 | 5.1 | 15.6 | 53.5 | 76.9 | 93.6 | 100.0 |
| 37° C./80% RH |  |  |  |  |  |  |  |  |  |
| 1 mo. | 12.42 | 262.6 | 2.1 | 6.1 | 12.6 | 35.1 | 56.2 | 75.1 | 86.1 |

The above results demonstrate that there was a profound slowing of the dissolution of hydromorphone HCl from the coated beads when the beads were subjected to accelerated storage conditions.

EXAMPLE 3

Protecting the Retardant Coating

In order to determine if the slowing of the dissolution of the hydromorphone beads of Example 2 was due to a stability problem between the hydromorphone and the retardant, in Example 3 Nu pariel hydromorphone beads were prepared according to Example 1, then overcoated with 5% HPMC, and tested without the retardant layer. Dissolution tests were conducted initially, and after storage at accelerated conditions of 37° C. dry and 37° C./80%RH.

The results of the dissolution tests for Example 3 are set forth in Table 4 below:

TABLE 4

Hydromorphone HCl 8 mg Controlled Release Capsules Stability Data Summary

| Testing Time | Hydromorphone HCl | Average Weight (mg) | 1 hr | 2 hr |
|---|---|---|---|---|
| Initial | 8.49 | 166 | 100.0 | 100.0 |
| 37° C. dry | | | | |
| 1 mo. | 8.49 | 167 | 100.0 | 100.0 |
| 2 mo. | 8.49 | 167 | 100.0 | 100.0 |
| 37° C./80% RH | | | | |
| 1 mo. | 8.49 | 167 | 100.0 | 100.0 |
| 2 mo. | 8.49 | 170.3 | 100.0 | 100.0 |

The results of Example 3 show that the coated beads which did not include a retardant coating were stable.

In order to determine the relative humidity under "dry conditions" in the oven, the relative humidity in a water-filled desiccator in a 60° C. oven was determined as follows. First, about 500 grams of purified water is poured into a plastic desiccator and the metal guard inserted. A hygrometer/temperature indicator is placed on top of the guard and the desiccator covered and placed in the 60° C. oven for 24 hours. After 24 hours the relative humidity in the desiccator was 85% while the temperature was still 60° C. On placing the hygrometer alone in the 60° C. oven for 24 hours, the relative humidity was 9% at 60° C.

EXAMPLE 4

Prior Art Curing (According to Literature Recommendations)

In Example 4, hydromorphone beads prepared according to Example 3 were coated with the Eudragit ® RS to a 5% weight gain. After application of the coating, the beads were dried (cured) at 45° C. in a fluidized bed dryer for 2 hours. This temperature is above the Tg of Eudragit ® RS 30D, plasticized with Triethylcitrate at 20% level of solids. Dissolution tests were conducted initially, and after storage at 37° C. dry and 37° C./80%RH. The results are set forth in Table 5 below:

TABLE 5

Hydromorphone HCl 8 mg Controlled Release Capsules Stability Data Summary

| Testing Time | Hydromorphone HCl | Average Weight (mg) | 1 hr | 2 hr | 4 hr | 8 hr | 12 hr | 18 hr | 24 hr |
|---|---|---|---|---|---|---|---|---|---|
| 2 hours* | 8.50 | 178.5 | 8.0 | 21.8 | 45.7 | 79.3 | 94.2 | | |
| 37° C. dry | | | | | | | | | |
| 1 mo. | 8.50 | 177 | 16.8 | 25.8 | 44.2 | 67.8 | 80.8 | | |
| 2 mo. | 8.39 | 174 | 24.6 | 40.8 | 61.8 | 83.4 | 94.0 | 100.0 | |
| 37° C./80% RH | | | | | | | | | |
| 1 mo. | 8.50 | 174 | 48.8 | 60.1 | 80.7 | 94.0 | 100.0 | | |
| 2 mo. | 8.55 | 178 | 53.6 | 76.3 | 90.7 | 98.2 | 100.0 | | |

*initial dissolution after curing

From the results provided above, it can be seen that the hydromorphone dissolution from the beads underwent significant changes upon storage, and that the short curing step recommended in the literature and utilized in Example 4 did not to help the stability/curing problem.

EXAMPLES 5-6

Protecting The Retardant Coating

In Example 5, Eudragit ®-coated beads prepared according to Example 4 were overcoated with 5% HPMC to protect the retardant coating from the environment. Dissolution tests were conducted initially, after storage at room temperature (RT) for 3 months, and after storage at 37° C. dry and 37° C./80%RH. The results are set forth in Table 6 below:

TABLE 6

Hydromorphone HCl 8 mg Controlled Release Capsules Stability Data Summary

| Testing Time | Hydromorphone HCl | Average Weight (mg) | 1 hr | 2 hr | 4 hr | 8 hr | 12 hr | 18 hr | 24 hr |
|---|---|---|---|---|---|---|---|---|---|
| Initial | 8.29 | 180.5 | 6.9 | 17.2 | 37.5 | 65.8 | 80.2 | 100.0 | |
| RT | | | | | | | | | |
| 3 mo. | 8.42 | 178.3 | 9.4 | 17.9 | 63.1 | 81.6 | 91.8 | 97.2 | |
| 37° C. dry | | | | | | | | | |
| 1 mo. | 8.29 | 182 | 6.4 | 12.5 | 28.6 | 63.9 | 85.7 | 100.0 | |
| 2 mo. | 8.56 | 175 | 8.1 | 15.4 | 31.3 | 61.9 | 78.5 | 89.4 | |
| 3 mo. | 8.30 | 177 | 6.8 | 14.2 | 30.3 | 61.4 | 77.8 | 89.8 | |
| 37° C./80% RH | | | | | | | | | |
| 1 mo. | 8.29 | 186.7 | 7.9 | 15.7 | 34.8 | 68.4 | 88.0 | 100.0 | |
| 2 mo. | 8.41 | 182 | 9.7 | 17.6 | 35.2 | 66.0 | 83.2 | 94.7 | |
| 3 mo. | 8.78 | 181.7 | 6.4 | 12.2 | 28.2 | 59.7 | 77.3 | 88.4 | |

In Example 6, Eudragit ®-coated beads prepared according to Example 4 which were not cured were overcoated with 5% HPMC to protect the retardant coating from the environment. Dissolution tests were conducted initially, and after storage at 37° C. dry and 37° C./80%RH. The results are set forth in Table 7 below:

TABLE 7

Hydromorphone HCl 8 mg Controlled Release Capsules Stability Data Summary

| Time | Hydromorphone HCl | Average Fill Wt (mg) | 1 hr | 2 hr | 4 hr | 8 hr | 12 hr | 18 hr | 24 hr |
|---|---|---|---|---|---|---|---|---|---|
| Initial | 8.28 | 178.3 | 10.7 | 10.5 | 34.0 | 68.3 | 85.1 | | |
| RT | | | | | | | | | |
| 3 mo. | 8.32 | 177 | 5.5 | 10.5 | 21.5 | 57.3 | 77.9 | 92.5 | |
| 37° C. dry | | | | | | | | | |
| 1 mo. | 8.28 | 178 | 1.4 | 2.4 | 6.2 | 27.3 | 61.8 | | |
| 2 mo. | 8.39 | 177 | 2.0 | 6.3 | 12.6 | 38.5 | 70.2 | 84.6 | |
| 3 mo. | 8.20 | 172 | 1.1 | 4.1 | 8.8 | 30.3 | 61.2 | 84.6 | |
| 37° C./80% RH | | | | | | | | | |
| 1 mo. | 8.28 | 176.7 | 2.3 | 4.0 | 9.3 | 32.7 | 61.4 | | |
| 2 mo. | 8.70 | 179 | 2.6 | 6.5 | 11.1 | 35.2 | 66.6 | 90.1 | |
| 3 mo. | 8.26 | 177 | 1.3 | 4.1 | 9.3 | 30.4 | 62.3 | 87.7 | |

As can be seen from the results provided in Tables 6 and 7, other than preventing the spheroids (particularly the Eudragit ® coated spheroids) from agglomerating at accelerated conditions, the terminal HPMC overcoat did not stabilize the products of Examples 5 and 6. On the basis of these results, however, it was hypothesized that, despite the fact that the dissolution changed under accelerated conditions, the cured endpoint could be reached at either dry or moist conditions at 37° C.

EXAMPLES 7-9

Optimizing Curing and Ingredients of Retardant Coating

The results obtained from Examples 2-7 indicated that the dissolution of the beads overcoated with a retardant coating seemed to slow down to a point and no further. However, the endpoint dissolutions achieved were too slow.

Since the hydromorphone in the formulations had been protected from the environment, it was hypothesized that exposure to accelerated conditions (e.g., 37° C./80%RH) had the effect of further "curing" the retardant layer. Additional tests were therefore conducted to determine processing conditions required during manufacture to cure the product to its endpoint dissolution.

In order to obtain a formulation having a more suitable dissolution curve, and, rather than reduce the coating to less than 5% weight gain, the more soluble Eudragit ® RL (methacrylic ester 1:20 quaternary ammonium groups) was included in the retardant coat.

In Examples 7-9, the hydromorphone beads prepared pursuant to Example 5. In Example 7, the retardant coating consisted of 100% Eudragit ® RL. In Example 8, the retardant coating consisted of 50% Eudragit ® RL and 50% Eudragit ® RS. Finally, In Example 9, the retardant coating consisted of 10% Eudragit ® RL: Eudragit ® 90% RS. Each of Examples 7-9 were coated to total weight gain of 5%.

Each of the HPMC-protected coatings of Examples 7-9 were cured to 1, 2, 7, 10, 21 and 30 days at 45° C. dry, at which times dissolution studies as set forth in Example 2 were conducted.

Only Example 9 showed a desirable release profile, and curing was complete after only one day. Dissolution studies of the products of Examples 7 and 8 showed the same to be immediate release products, the amount-/type of retardant used not being sufficient to prevent immediate release of the drug (i.e., about 100% of the drug being released after one hour), even after the formulations were cured. Example 9 was further tested by storing under accelerated conditions as follows. After curing for 21 days, the samples of Example 9 were placed in a 37° C./80%RH oven, and dissolution tests as set forth in Example 2 were conducted after 7 and 30 days. Representative dissolution profiles for Example 9 (mean results for three samples) are set forth in Table 8 below:

TABLE 8

Hydromorphone HCl 8 mg MD CR Eudragit ® 5% Beads

| Curing Time | Wt (mg) | Percent Hydromorphone HCl Dissolved | | | | | | |
|---|---|---|---|---|---|---|---|---|
| | | 1 hr | 2 hr | 4 hr | 8 hr | 12 hr | 18 hr | 24 hr |
| Initial Mean | 191 | 16.6 | 53.1 | 69.3 | 86.7 | 95.6 | 99.3 | 100.0 |
| 1 day Mean | 190.7 | 7.1 | 33.1 | 66.6 | 87.3 | 99.5 | 97.9 | 99.0 |
| 2 days Mean | 190.7 | 7.4 | 35.0 | 67.0 | 87.4 | 95.1 | 98.4 | 99.2 |
| 7 days Mean | 190.7 | 8.0 | 36.3 | 67.7 | 86.6 | 93.3 | 96.8 | 98.4 |
| 10 days Mean | 191.3 | 7.2 | 36.5 | 68.9 | 88.5 | 94.8 | 98.0 | 99.5 |
| 21 days Mean | 191 | 6.9 | 36.1 | 66.9 | 86.2 | 92.7 | 99.8 | 99.0 |
| 30 days Mean | 190.3 | 5.83 | 31.9 | 65.2 | 82.7 | 90.4 | 96.3 | 96.7 |

TABLE 8-continued

Hydromorphone HCl 8 mg MD CR Eudragit ® 5% Beads

| Curing Time | Wt (mg) | Percent Hydromorphone HCl Dissolved | | | | | | |
|---|---|---|---|---|---|---|---|---|
| | | 1 hr | 2 hr | 4 hr | 8 hr | 12 hr | 18 hr | 24 hr |
| Storage Time/Conditions 30° C./80% RH | | | | | | | | |
| 7 days Mean | 190.7 | 5.9 | 25.1 | 62.7 | 84.6 | 92.6 | 97.6 | 99.5 |
| 30 days Mean | 190.3 | 5.8 | 31.9 | 65.2 | 82.7 | 90.4 | 96.3 | 96.9 |

The results set forth in Table 8 demonstrate that the 1 month dissolution profile showed no slowdown as compared to the initial cured sample, even for the samples tested under accelerated conditions. Thus, after curing for 24 hours at 45° C., the methacrylate controlled release film coating was essentially stabilized.

EXAMPLES 10-12

Optimizing Retardant Coating Thickness

In Examples 10-12, additional experimentation was conducted to determine the optimum weight of methacrylate polymer to use for a desirable release profile and to determine reproducibility and effectiveness of the 48 hour curing step at 45° C. dry. Three batches were manufactured at different levels of methacrylate load and cured in a 45° C. dry oven.

In Example 10, hydromorphone beads were prepared in accordance with those of Example 3, as set forth in Table 9 below:

TABLE 9

Hydromorphone HCl MD Beads

| Ingredients | Percent (by wt) | Amt/Unit (mg) |
|---|---|---|
| Hydromorphone HCl | 4.75% | 4 |
| Nupariels Pa 18/20 | 87.89% | 74 |
| Opadry Lt Pink Y-5-1442 | 2.38% | 2 |
| Opadry Lt Pink Y-5-1442 | 4.99% | 4.2 |
| | 100% | 84.2 |

The hydromorphone beads were then further processed in accordance with Example 5. In Example 10, the retardant coating was Eudragit ® RS, Eudragit ® RL 90:10 (5% w/w coating). The formula for Example 10 is set forth in Table 10 below:

TABLE 10

Hydromorphone HCl MD CR Eudragit ® 5% Beads

| Ingredients | Percent (by wt) | Amt/Unit (mg) |
|---|---|---|
| Hydromorphone beads | 87.96% | 84.2 mg |
| Eudragit ® RS 30D (90%) | 3.97% | 3.8 mg |
| Eudragit ® RL 30D (10%) | 0.42% | 0.4 mg |
| TEC (20% of RS & RL) | 0.88% | 0.84 mg |
| Talc (40% of RS & RL) | 1.75% | 1.68 mg |
| Purified water | | qs |
| Opadry Lt Pink Y-5-1442 | 5.01% | 4.8 |
| | 100% | 95.72 mg |

Examples 11 and 12 are prepared in similar fashion to Example 10. In Example 11, the retardant coating was Eudragit ® RS, Eudragit ® RL 90:10 (8% w/w coating). In Example 12, the retardant coating was Eudragit ® RS, Eudragit ® RL 90:10 (12% w/w coating). The formulas for Examples 11 and 12 are set forth in Tables 11 and 12, respectively, below:

TABLE 11

Hydromorphone HCl MD CR Eudragit ® 8% Spheres

| Ingredients | Percent (by wt) | Amt/Unit (mg) |
|---|---|---|
| Hydromorphone beads | 84.2% | 84.2 |
| Eudragit ® RS 30D (90%) | 6.07% | 6.07 |
| Eudragit ® RL 30D (10%) | 0.67% | 0.67 |
| TEC 20% of RS & RL) | 1.35% | 1.35 |
| Talc (40% of RS & RL) | 2.70% | 2.70 |
| Purified water | | qs |
| Opadry Lt Pink Y-5-1442 | 5.0% | 5.0 |
| | 99.99% | 99.99 |

TABLE 12

Hydromorphone HCl MD CR Eudragit ® 12% Spheres

| Ingredients | Percent (by wt) | Amt/Unit (mg) |
|---|---|---|
| Hydromorphone beads | 79.69% | 84.2 |
| Eudragit ® RS 30D (90%) | 8.61% | 9.1 |
| Eudragit ® RL 30D (10%) | 0.95% | 1.0 |
| TEC (20% of RS & RL) | 1.91% | 2.02 |
| Talc (40% of RS & RL) | 3.82% | 4.04 |
| Purified water | | qs |
| Opadry Lt Pink Y-5-1442 | 5.02% | 5.3 |
| | 100% | 105.66 |

Each of Examples 10–12 were cured on paper lined trays in a 45° C. oven for two days after the application of the Eudragit ® Controlled Release Coating and the HPMC 5% overcoating. Dissolution studies were then conducted on Examples 10–12.

Initial dissolution profiles (after curing) of Example 10 showed it to resemble Example 9 (the products of both Examples were overcoated with a 5% w/w Eudragit ® coating). After curing for 2 days, samples of Example 10 were subjected to further tests at room temperature, and under accelerated conditions of 37° C./80%RH, 37° C. dry and 50° C. dry. Representative dissolution profiles for Example 10 (mean results for three samples) are set forth in Table 13 below:

TABLE 13

Hydromorphone HCl CR 8 mg Eudragit ® 5% Capsules
Percent Hydromorphone HCl Dissolved

| Time | Wt (mg) | 1 hr | 2 hr | 4 hr | 8 hr | 12 hr | 18 hr | 24 hr |
|---|---|---|---|---|---|---|---|---|
| 2 days* Mean RT | 191.3 | 6.3 | 36.2 | 69.3 | 87.8 | 97.3 | 100.0 | |
| 1 mo. Mean 37° C./80% RH | 191.1 | 6.0 | 30.8 | 63.1 | 83.4 | 91.8 | 96.3 | 97.9 |
| 1 mo. Mean | 191.6 | 6.9 | 28.5 | 63.2 | 84.5 | 91.5 | 95.6 | 97.8 |
| 2 mo. Mean 37° C. Dry | 194.3 | 11.4 | 35.6 | 70.7 | 90.5 | 96.8 | 100 | |
| 1 mo. Mean 50° C. Dry | 192.0 | 11.4 | 35.1 | 68.6 | 87.9 | 94.5 | 98.9 | 100 |
| 1 mo. Mean | 191.4 | 11.1 | 41.4 | 70.6 | 90.4 | 96.5 | 100 | |
| Comparison to Example 9 (1 day and 2 day dissolutions) | | | | | | | | |
| 1 day Mean | 190.7 | 7.1 | 33.1 | 66.6 | 87.3 | 99.5 | 97.9 | 99.0 |
| 2 Days Mean | 190.7 | 7.4 | 35.0 | 67.0 | 87.4 | 95.1 | 98.4 | 99.2 |

*initial dissolution after curing

As can be seen from the dissolution results provided for Example 10, although the dissolution profile of the samples were not taken after 1 day of curing, the results obtained after 2 day curing are substantially similar to the results obtained for the 1 and 2 day curings of Example 9. Therefore, it is hypothesized that the product of Example 10 was also stable after one day curing.

After curing for 2 days, samples of Example 11 were tested for dissolution, and then samples of Example 11 were exposed to accelerated conditions of 37° C./80%RH for one month. Representative initial dissolution profiles (mean results for three samples) for Example 11 are set forth in Table 14 below:

TABLE 14

Hydromorphone HCl CR 8 mg Eudragit ® 8% Capsules
Percent Hydromorphone HCl Dissolved

| Time | Wt (mg) | 1 hr | 2 hr | 4 hr | 8 hr | 12 hr | 18 hr | 24 hr |
|---|---|---|---|---|---|---|---|---|
| 2 days* Mean 37° C./80% RH | 201.3 | 0.8 | 3.3 | 40.0 | 78.4 | 90.7 | 97.5 | 99.9 |
| 1 mo. Mean | 7.3 | 8.6 | 34.1 | 72.8 | 85.5 | 93.2 | 97.2 | |

*initial dissolution after curing

As can be seen from the dissolution results provided above for Example 11, the results obtained after 2 day curing are substantially similar to the results obtained under accelerated storage conditions of 37° C./80%RH, thus indicating the stability of Example 11 after a 2 day curing. Furthermore, the dissolution results obtained with Example 11 showed slower release rates of hydromorphone, as would be expected given the thicker retardant coating.

After curing for 2 days, samples of Example 12 were tested for dissolution, and then samples of Example 12 were subjected to further tests after storing for one month at room temperature, and under accelerated conditions of 37° C./80%RH, 37° C. dry and 50° C. dry. Representative dissolution profiles (mean results for three samples) for Example 12 are set forth in Table 15 below:

TABLE 15

Hydromorphone HCl CR 8 mg Eudragit ® 12% Capsules
Percent Hydromorphone HCl Dissolved

| Time | Wt (mg) | 1 hr | 2 hr | 4 hr | 8 hr | 12 hr | 18 hr | 24 hr |
|---|---|---|---|---|---|---|---|---|
| 2 days* Mean RT | 215.3 | 0.8 | 3.1 | 9.3 | 70.9 | 90.4 | 100.8 | 104.8 |
| 1 mo. Mean 37° C./80% RH | 210.8 | 0 | 1.8 | 4.6 | 62.9 | 84.3 | 96.1 | 99.8 |
| 1 mo. Mean 37° C. Dry | 213.8 | 2.2 | 4.8 | 7.2 | 50.8 | 74.3 | 87.3 | 93.3 |
| 1 mo. Mean 50° C. Dry | 210.4 | 0.8 | 2.2 | 6.9 | 59.7 | 82.2 | 96.3 | 100 |
| 1 mo. Mean | 207.3 | 1.6 | 1.5 | 3.3 | 51.5 | 76.2 | 90.9 | 97.4 |

*initial dissolution after curing

As can be seen from the dissolution results provided above for Example 12, the dissolution results obtained with Example 12 showed slower release rates of hydromorphone as compared to the thinner retardant coatings of Examples 10 and 11, as expected. The overall results obtained after 2 day curing are substantially similar to the results obtained under accelerated storage conditions of 37° C./80%RH, with the exception of the percent drug dissolved at the 8 hour and 12 hour points. These results might indicate that at high loads of retardant coating, it may be necessary to cure the coating for a longer period of time to attain a stabilized formulation.

EXAMPLE 13

Morphine Sulfate Coated Beads

In Example 13, the curing step of the present invention was applied to a formulation in which morphine sulfate was substituted as the drug.

A suspension of morphine sulfate and HPMC (Opadry ® Clear Y-5-7095) was applied onto 18/20 mesh nupariel beads in a fluid bed dryer with a Wurster insert at an inlet temperature of 60° C. An Opadry ® Lavender YS-1-4729 HPMC Base filmcoating suspension was then applied after drug loading as a protective coat at a 5% weight gain.

After the overcoating process was completed, the morphine sulfate beads were then overcoated with a retardant coating mixture of Eudragit ® RS 30D and Eudragit ® RL 30D at a ratio of 90:10, RS to RL, at a 5% weight gain level. The application of this mixture of Eudragit ® RS 30D and Eudragit ® RL 30D along with talc (included as an anti-tacking agent) and triethyl citrate (plasticizer) was done at an inlet temperature of 35° C. in a Wurster Insert.

Once the retardant overcoating was complete, the morphine sulfate beads were given a final overcoating of Opadry ® lavender YS-1-4729 at a 5% weight gain level.

After completion of the final filmcoating process, the morphine sulfate beads were cured on paper lined trays in a 45° C. dry oven for 2 days. After curing, the beads were filled into gelatin capsules at a 30 mg morphine sulfate strength. The final formula is provided in Table 16 below:

TABLE 16

| Processing Step | Ingredient | Mg/Capsule |
|---|---|---|
| Drug Load | Morphine Sulfate | 30 mg |
| | Nupariel PG 18/20 | 255 mg |
| | Opadry ® Clear Y-5-7095 | 15 mg |
| First Overcoat | Opadry ® Lavender YS-1-4729 | 15.8 mg |
| Retardant Overcoat | Eudragit ® RS 30D | 14.2 mg |
| | Eudragit ® RL 30D | 1.6 mg |
| | Triethylcitrate | 3.2 mg |
| | Talc | 6.3 mg |
| Final Overcoat | Opadry ® Lavender YS-1-4729 | 18.0 mg |
| | Total: | 359.1 mg |

Dissolution stability studies were then conducted on the product of Example 13 after the above-mentioned curing step at storage conditions of room temperature, 37° C./80%RH, 37° C. dry, and 50° C. dry after one month and after two months. The results are set forth in Table 17 below:

TABLE 17

Morphine Sulfate CR 30 mg Eudragit ® 5% Capsules
Percent Morphine Sulfate Dissolved

| Time | 1 hr | 2 hr | 4 hr | 6 hr | 8 hr | 12 hr | 18 hr | 24 hr |
|---|---|---|---|---|---|---|---|---|
| 2 days* Mean | 0.0 | 43.5 | 74.9 | — | 91.8 | 95.3 | 99.8 | 100 |
| RT | | | | | | | | |
| 1 mo. Mean | 0.0 | 36.9 | 73.8 | 86.9 | 92.2 | 96.5 | 99.9 | 100 |
| 2 mo. Mean | 2.0 | 37 | 72 | 82 | 88 | 92 | 96 | 99 |
| 37° C./80% RH | | | | | | | | |
| 1 mo. Mean | 0.0 | 28.4 | 70.3 | 84.8 | 92.1 | 97.7 | 100 | |
| 2 mo. | 1.9 | 30.1 | 68.4 | 79.9 | 87.0 | 93.5 | 95.6 | 97.8 |

TABLE 17-continued

Morphine Sulfate CR 30 mg Eudragit ® 5% Capsules
Percent Morphine Sulfate Dissolved

| Time | 1 hr | 2 hr | 4 hr | 6 hr | 8 hr | 12 hr | 18 hr | 24 hr |
|---|---|---|---|---|---|---|---|---|
| Mean 37° C. Dry | | | | | | | | |
| 1 mo. Mean | 0.0 | 32.0 | 72.5 | 86.0 | 93.2 | 97.3 | 100 | |
| 2 mo. Mean | 0.9 | 26.4 | 67.5 | 78.8 | 88.6 | 94.0 | 98.0 | 99.5 |
| 50° C. Dry | | | | | | | | |
| 1 mo. Mean | 0.0 | 37.7 | 74.1 | 89.3 | 93.7 | 98.5 | 100 | |
| 2 mo. Mean | 2.0 | 33.0 | 74 | 85 | 94 | 98 | 100 | |

*initial dissolution after curing

The results set forth in Table 17 demonstrate that the curing process stabilized the dissolution profile of the morphine sulfate to an endpoint dissolution rate which substantially remained constant, even for the samples stored under accelerated conditions.

The examples provided above are not meant to be exclusive. Many other variations of the present invention would be obvious to those skilled in the art, and are contemplated to be within the scope of the appended claims.

What is claimed is:

1. A method for obtaining a stabilized controlled release formulation comprising a substrate coated with an aqueous dispersion of a plasticized acrylic polymer for release of a dose of therapeutically active agent in the gastrointestinal tract, comprising
preparing a solid substrate comprising a therapeutically active agent,
overcoating said substrate with a sufficient amount of a plasticized aqueous dispersion consisting essentially of ammonio methacrylate copolymers which are copolymerizates of acrylic and methacrylic esters having a low content of quaternary ammonium groups acrylic and methacrylic acid esters having a permeability which is unaffected by the pH conditions prevailing in the gastrointestinal tract, in an amount sufficient to obtain a predetermined controlled release of said dose of said therapeutically active agent in the gastrointestinal tract, and
curing said coated substrate by subjecting said coated substrate to a temperature greater than the glass transition temperature of the aqueous dispersion of plasticized acrylic polymer for at least about 24 hours and continuing the curing until an endpoint is reached at which said substrate provides a stable dissolution profile, said endpoint being determined by comparing the dissolution profile of the formulation immediately after curing to the dissolution profile of the formulation after exposure to accelerated conditions of one month at a temperature of 37° C. and at a relative humidity of 80%.

2. The method of claim 1, further comprising determining the endpoint for the formulation by exposing the formulation which is uncured or substantially uncured to stressed storage conditions and obtaining dissolution profiles for the formulation until the dissolution profiles of the formulation are substantially stabilized.

3. The method of claim 2, further comprising modifying the formulation to obtain a desired dissolution profile of said therapeutically active agent based on said end point.

4. The method of claim 1, further comprising preparing said substrate for oral administration by coating said therapeutically active agent onto the surface of pharmaceutically acceptable beads, and preparing an oral dosage form by placing a sufficient quantity of cured coated beads into a capsule.

5. The method of claim 1, further comprising preparing said substrate for oral administration by incorporating said therapeutically active agent into a tablet.

6. The method of claim 1, wherein said acrylic polymer is prepared by mixing a first copolymer of acrylic and methacrylic and esters having a molar ratio of ammonium groups to (meth)acrylic esters of about 1:20 with a second copolymer of acrylic and methacrylic esters having a molar ratio of ammonium groups to (meth)acrylic esters of about 1:40, with a suitable plasticizing agent.

7. The method of claim 1, wherein said coated substrate is cured for a time period from about 24 to about 48 hours.

8. The method of claim 1 wherein said coated substrate is cured for about 48 hours.

9. The method of claim 1, wherein said therapeutically active agent is selected from the group consisting of antihistamines, analgesics, non-steroidal anti-inflammatory agents, gastro-intestinals, anti-emetics, anti-epileptics, vasodilators, anti-tussive agents, expectorants, anti-asthmatics, hormones, diuretics, anti-hypotensives, bronchodilators, antibiotics, antihemorrhoidals, hypnotics, psychotropics, antidiarrheals, mucolytics, sedatives, decongestants, laxatives, vitamins, and stimulants.

10. The method of claim 1, wherein said therapeutically active agent is selected from the group consisting of hydromorphone, oxycodone, dihydrocodeine, codeine, dihydromorphine, morphine, buprenorphine, salts of any of the foregoing, and mixtures of any of the foregoing.

11. The method of claim 1, wherein said therapeutically active agent is theophylline.

12. The stabilized product prepared according to the method of claim 1.

13. The stabilized product prepared according to the method of claim 4.

14. The stabilized product prepared according to the method of claim 5.

15. A stabilized controlled release solid dosage form for release of a dose of a therapeutically active agent comprising a substrate comprising a therapeutically active agent, said substrate overcoated with an aqueous dispersion consisting essentially of a plasticized copolymer of acrylic and methacrylic acid esters having a permeability which is unaffected by the pH conditions prevailing in the digestive tract, in an amount sufficient to provide a controlled release of said dose of therapeutically active agent in the gastrointestinal tract, said coated substrate being cured at a temperature greater than the glass transition temperature of the aqueous dispersion of the plasticized acrylic polymer for at least about 24 hours, until an endpoint is reached at which the coated substrate provides a stable dissolution profile, said endpoint being determined by comparing the dissolution profile of the formulation immediately after curing to the dissolution profile of the formulation after exposure to accelerated conditions of one month at a temperature of 37° C. and at a relative humidity of 80%.

16. The stabilized controlled release solid dosage form of claim 15, wherein said therapeutically active agent is overcoated with said aqueous dispersion of plasticized ammonio acrylic polymer to a weight gain level from about 5 to about 15 percent.

17. The stabilized controlled release solid dosage form of claim 15, wherein said acrylic polymer coating is derived from a mixture of a first copolymer of acrylic and methacrylic acid esters having a molar ratio of ammonium groups to (meth)acrylic esters of about 1:20 and a second copolymer of acrylic and methacrylic esters having a molar ratio of ammonium groups to (meth)acrylic esters of about 1:40, the ratio of said first copolymer to said second copolymer being from about 10:90 to about 90:10.

18. The stabilized controlled release solid dosage form of claim 15, wherein said substrate comprises an inert pharmaceutically acceptable bead onto which said therapeutically active agent is coated.

19. The stabilized controlled release solid dosage form of claim 18, wherein a plurality of said coated, cured beads are placed in a capsule in an amount sufficient to provide an effective controlled release dose when contacted by an gastric and intestinal fluid.

20. The stabilized controlled release solid dosage form of claim 15 which has been cured for a time period from about 24 to about 48 hours.

21. The stabilized controlled release solid dosage form of claim 15 which has been cured for about 48 hours.

22. The stabilized controlled release solid dosage form of claim 15, wherein said substrate is compressed with or without additional inert ingredients into a tablet.

23. The stabilized controlled release solid dosage form of claim 15, wherein said therapeutically active agent is selected from the group consisting of antihistamines, analgesics, non-steroidal anti-inflammatory agents, gastro-intestinals, anti-emetics, anti-epileptics, vasodilators, anti-tussive agents, expectorants, anti-asthmatics, hormones, diuretics, anti-hypotensives, bronchodilators, antibiotics, antihemorrhoidals, hypnotics, psychotropics, antidiarrheals, mucolytics, sedatives, decongestants, laxatives, vitamins, and stimulants.

24. The stabilized controlled release solid dosage form of claim 15, wherein said therapeutically active agent is selected from the group consisting of hydromorphone, oxycodone, dihydrocodeine, codeine, dihydromorphine, morphine, buprenorphine, salts of any of the foregoing, and mixtures of any of the foregoing.

25. The stabilized controlled release solid dosage form of claim 15, wherein said therapeutically active agent is theophylline.

26. A stabilized controlled release solid dosage form comprising
   a substrate comprising inert pharmaceutically acceptable beads onto which a therapeutically active agent is coated,
   said substrate overcoated with an aqueous dispersion consisting essentially of a plasticized ammonio methacrylate copolymer derived from a mixture of a first copolymer of acrylic and methacrylic esters having a molar ratio of ammonium groups to (meth)acrylic esters of about 1:20 and a second copolymer of acrylic and methacrylic esters having a molar ratio of ammonium groups to (meth)acrylic esters of about 1:40, said first and second copolymers having a permeability which is unaffected by the pH conditions prevailing in the gastrointestinal tract, the ratio of said first copolymer to said second copolymer being from about 10:90 to about 90:10, said substrate being coated to a weight gain level from about 5 to about 15 percent and the amount of said ammonio methacrylate copolymer being sufficient to provide a predetermined controlled release of said therapeutically active agent in the gastrointestinal tract, the coated substrate cured at a temperature greater than the glass transition temperature of the aqueous dispersion of the plasticized acrylic polymer for at least about 24 hours, until an endpoint is reached at which said coated substrate provides a stable in-vitro release of said therapeutically active agent when exposed to accelerated storage conditions of one month at 37° C. and 80% relative humidity.

27. The stabilized controlled release solid dosage form of claim 26 which has been cured for a time period from about 24 to about 48 hours.

28. The stabilized controlled release solid dosage form of claim 26 which has been cured for about 48 hours.

29. The stabilized controlled release solid dosage form of claim 26, wherein said substrate is compressed with or without additional inert ingredients into a tablet.

30. The stabilized controlled release solid dosage form of claim 26, wherein said therapeutically active agent is selected from the group consisting of hydromorphone, oxycodone, dihydrocodeine, codeine, dihydromorphine, morphine, buprenorphine, and salts of any of the foregoing.

31. The stabilized controlled release solid dosage form of claim 26, wherein a plurality of said coated, cured beads are placed in a capsule in an amount sufficient to provide an effective controlled release dose when contacted by an aqueous solution.

32. The stabilized controlled release solid dosage form of claim 26, wherein said therapeutically active agent is selected from the group consisting of antihistamines, analgesics, gastro-intestinals, anti-emetics, anti-epileptics, vasodilators, anti-tussive agents, expectorants, anti-asthmatics, hormones, diuretics, anti-hypotensives, bronchodilators, antibiotics, antihemorrhoidals, hypnotics, psychotropics, antidiarrheals, mucolytics, sedatives, decongestants, laxatives, vitamins, and stimulants.

33. The stabilized controlled release solid dosage form of claim 26, wherein said therapeutically active agent is theophylline.

34. A stabilized solid controlled release dosage form comprising a substrate comprising a therapeutically active agent, said substrate overcoated with a controlled release coating derived from an aqueous dispersion consisting essentially of a plasticized ammonio methacrylate copolymer, said ammonio methacrylate copolymer which is a copolymerizate of acrylic and methacrylic esters having a low content of quaternary ammonium groups being included in said coating in an amount sufficient to provide a controlled release of said therapeutically active agent in the gastrointestinal tract, said ammonio methacrylate copolymer having a permeability which is unaffected by the pH conditions prevailing in the gastrointestinal tract, said coated substrate being cured at a temperature above the glass transition temperature of the plasticized ammonio methacrylate copolymer for at least about 24 hours for a time period necessary to obtain a final product which provides a stable in-vitro release of said therapeutically active agent when exposed to accelerated storage conditions of one month at 37° C. and 80% relative humidity.

35. A stabilized controlled release solid dosage form for release of a dose of a therapeutically active agent, comprising a substrate comprising a therapeutically active agent, said substrate overcoated with a controlled release coating of an aqueous dispersion of a plasticized ammonio methacrylate copolymers which are copolymerizates of acrylic and methacrylic esters having a low content of quaternary ammonium groups in an amount sufficient to provide release of said dose of therapeutically active agent in the gastrointestinal tract, said ammonio methacrylate copolymer having a permeability which is unaffected by the pH conditions prevailing in the gastrointestinal tract, said acrylic polymer being cured at a temperature greater than the glass transition temperature of the aqueous dispersion of the plasticized acrylic polymer for at least about 24 hours until an endpoint is reached such that a final product is obtained which provides a reproducible, stabilized dissolution profile, said endpoint being determined by comparing the dissolution profile of the formulation immediately after curing to the dissolution profile of the formulation after exposure to accelerated conditions of one month at a temperature of 37° C. and at a relative humidity of 80%.

* * * * *